United States Patent [19]
Toyama et al.

[11] Patent Number: 5,608,815
[45] Date of Patent: Mar. 4, 1997

[54] DEVICE FOR TESTING AN IMAGE OF A TEST OBJECT

[75] Inventors: Koichi Toyama; Tatsuo Yamamura, both of Kanagawa, Japan

[73] Assignee: Fuji Electric Co., Ltd., Japan

[21] Appl. No.: 339,957

[22] Filed: Nov. 15, 1994

[30] Foreign Application Priority Data

Nov. 16, 1993 [JP] Japan ................................ 5-285419

[51] Int. Cl.⁶ ..................................................... G06K 9/00
[52] U.S. Cl. ........................... 382/142; 382/272; 382/274; 250/223 B; 348/127
[58] Field of Search ..................................... 382/141, 142, 382/312, 272, 274, 271, 149; 356/237, 239, 240, 394, 428; 250/223 B, 559.45; 348/125, 127, 69; 358/475

[56] References Cited

U.S. PATENT DOCUMENTS

| | | | |
|---|---|---|---|
| 4,827,351 | 5/1989 | Sakamoto | 382/274 |
| 4,972,393 | 11/1990 | Cochran et al. | 356/394 |
| 5,233,199 | 8/1993 | Toyama | 250/559 |
| 5,268,773 | 12/1993 | Park et al. | 358/475 |
| 5,305,391 | 4/1994 | Gomibuchi | 356/240 |

FOREIGN PATENT DOCUMENTS

| | | | |
|---|---|---|---|
| 0523664 | 11/1994 | European Pat. Off. | G01B 11/30 |
| 3205540 | 9/1991 | Japan | G01N 21/88 |

*Primary Examiner*—Jose L. Couso
*Assistant Examiner*—D. Richard Anderson, Jr.
*Attorney, Agent, or Firm*—Greer, Burns & Crain, Ltd.

[57] ABSTRACT

An image testing device captures an image of a test object using a TV camera and raster-scans the image to search the test object for a scratch or spot. The device protects its test precision from being deteriorated by lowered brightness of an illuminator and properly maintains the illuminator by outputting an alarm on detecting a lowering of the illuminator. To realize the capabilities of the image testing device, it comprises a brightness measure circuit, a general determination circuit, etc. The brightness measure circuit receives a multivalued gray image signal or image data from the frame memory through a switching unit, obtains an average value of picture elements in a brightness measure area in a test object image, and outputs it as a measured brightness signal. The general determination circuit corrects, in proportion to a measured brightness a binarization threshold for use in detecting a picture element indicating a defect. When the measured brightness is smaller than its threshold more frequently than a predetermined number of times, the general determination circuit outputs an abnormal brightness occurrence signal.

9 Claims, 8 Drawing Sheets

FIG. 1A
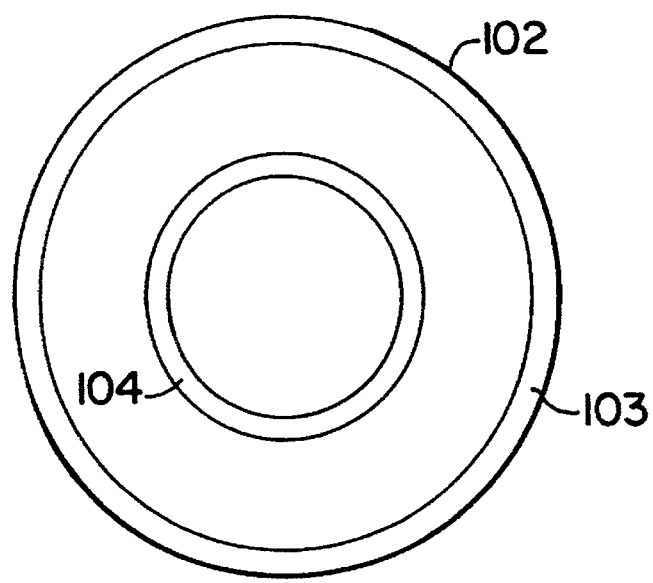
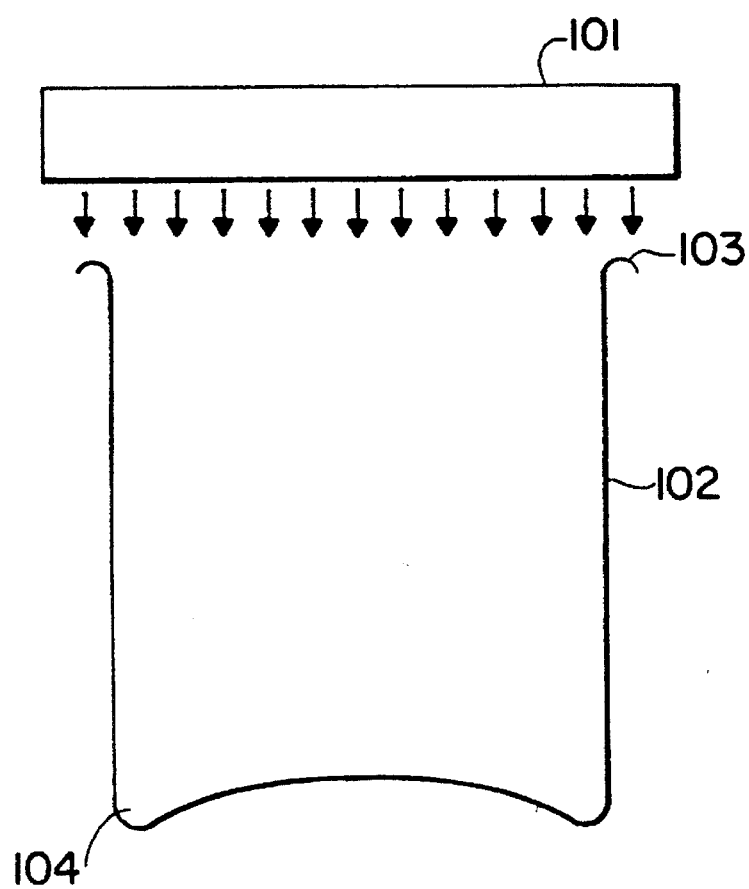
FIG. 1B

FIG. 2A
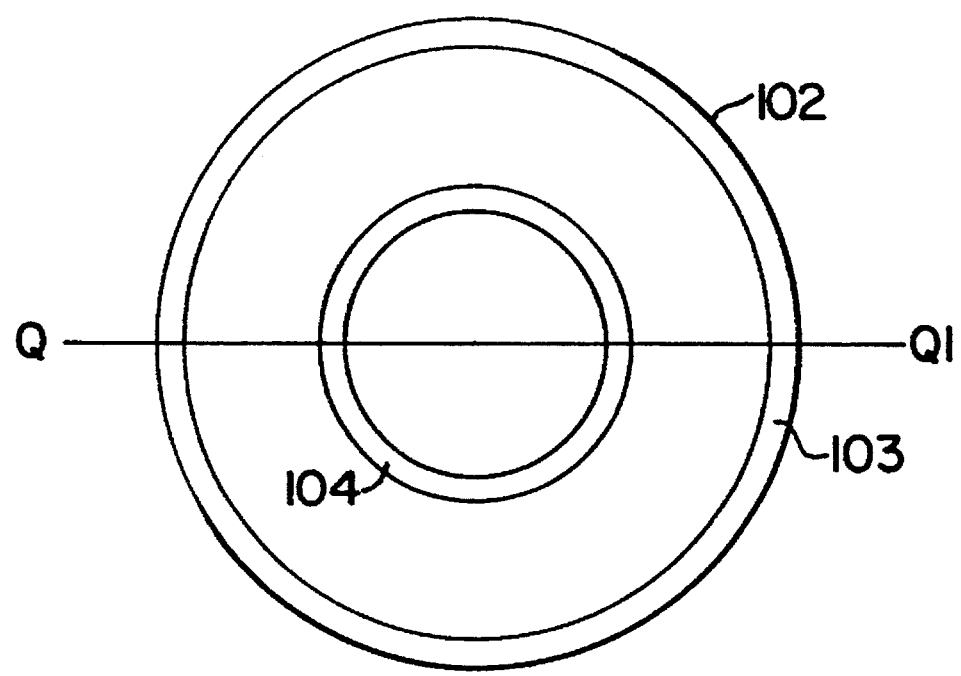
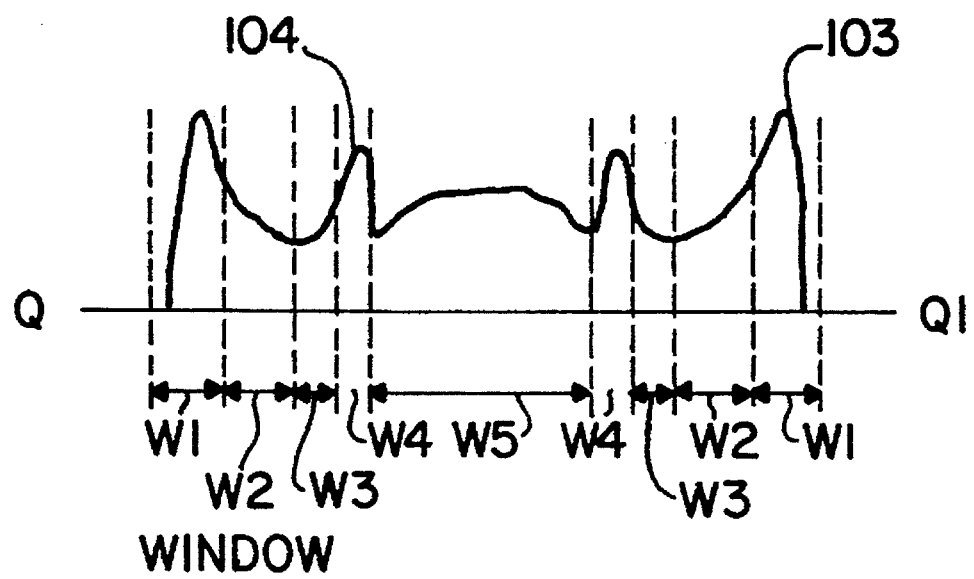
FIG. 2B

FIG. 7A
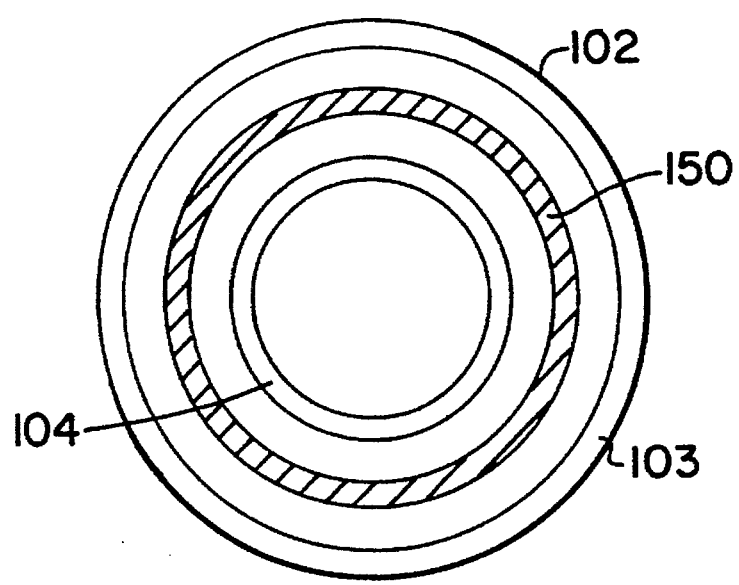
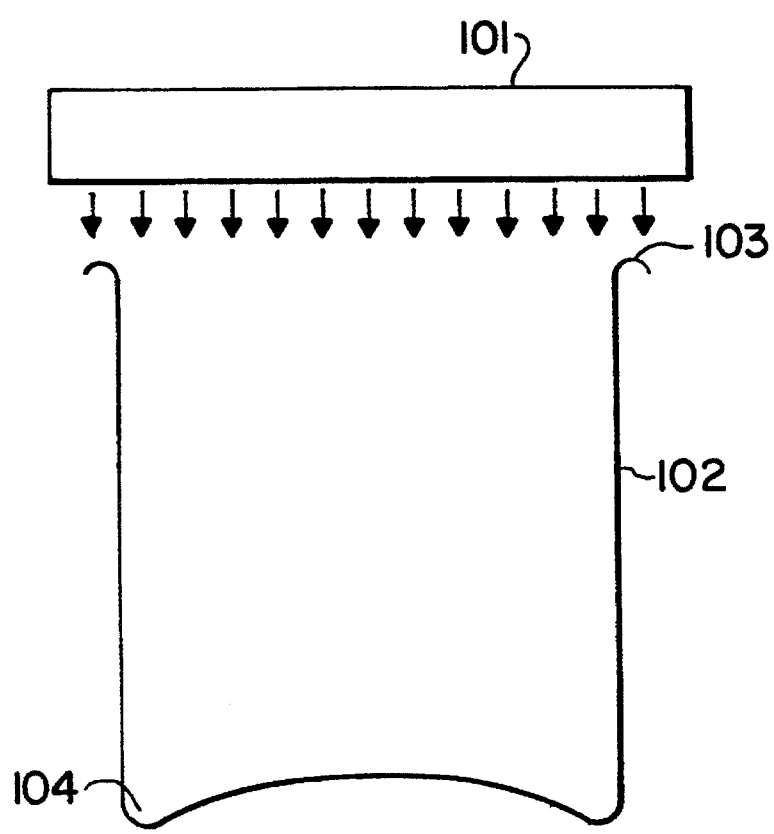
FIG. 7B

DEVICE FOR TESTING AN IMAGE OF A TEST OBJECT

BACKGROUND OF THE INVENTION

1. Field of the Invention

The present invention relates to an image testing device equipped with brightness measuring capabilities for testing an image of the inner surface of a cylindrical container as a test object which is transmitted by, for example, a conveyor so that foreign substances, dust, scratches, etc. can be successfully detected if they exist on the surface.

In the following figures, if units are assigned the same unit number, then the units are similar or correspond to each other.

2. Description of the Prior Art

FIGS. 1A and 1B show the method of observing a cylindrical container, that is, a test object, which has metallic luster on its inner surface. FIG. 1A is the top view of the cylindrical container, and FIG. 1B is its sectional view. 102 is a cylindrical container. A ring-shaped illuminator 101 illuminates the cylindrical container 102 from above, and the center axis of the illuminator 101 matches that of the cylindrical container 102. When a uniform ring-shaped light is provided by the illuminator 101, the light reflects off the inner surface having the metallic luster. Thus, when the test object is viewed from above, there are concentric light circles (hereinafter referred to as a brightness pattern) generated in the container. FIG. 1A shows a highlighted portion generated when the light of the illuminator directly reflects off the inner surface of the container. The strongest highlight can be detected around a highlighted opening 103 and a highlighted bottom 104.

FIG. 2A shows a scanning line Q-Q1 passing the center of the container shown in FIG. 1A. FIG. 2B shows a graph of the variation of gray levels inside the container along the scanning line Q-Q1. If the scanning line Q-Q1 is turned round the axis of the container, then a graph can be obtained as shown in FIG. 2B. The brightness pattern depends on a test object. The highlighted portion and a dark portion, which is generated when a light does not reflect off the surface toward the viewer, are different in respective cases. However, the feature of generating a concentric bright circle maintains. In the example shown in FIG. 2B, the inner surface of a cylindrical container can be divided into five areas W1 through W5 according to the variation of gray levels. The first area W1 refers to the highlighted opening 103. The second area W2 refers to the upper portion of the inner side of the container where the variation of gray levels is relatively small. The third area W3 receives a small amount of light from the illuminator 101 described by referring to FIG. 1, refers to the lower portion of the inner side of the container, and is darker than other portions. The fourth area W4 refers to the highlighted bottom 104. The fifth area W5 refers to the bottom portion.

With the conventional image testing device of a cylindrical container inner surface test device, each of these areas W1 through W5 is provided with a window, and a threshold is set to detect a defect indicated by a black spot and a white spot depending on the optical characteristics in each area. A method of detecting a defect is, for example, to binarize using a predetermined threshold an 8-bit multivalued gray image signal obtained by A/D converting an analog video signal (analog gray image signal) obtained by scanning an object image; to extract a defect signal by differentiating the video signal by a differentiation circuit as a differentiation method, etc. In the differentiation method, a differentiation signal is issued around the contour of the object. However, the differentiation generates either a forward pulse or a backward pulse around the contour of the object, and generates the forward and backward pulses simultaneously around a small defective portion. Using the above described feature of the differentiation method, a defective portion can be correctly extracted.

That is, assuming that the following expressions exist among point $P(i,j)$ at an object point (coordinate $x=i$, $y=j$) of a signal $P(x, y)$ obtained by differentiating the analog gray image signal based on a raster scanning; point $P(i-\alpha, j)$; and point $P(i+\beta, j)$ respectively positioned $\alpha$ picture elements before and $\beta$ picture elements after the object point in the x direction of the scanning line:

$P(i, j)-P(i-\alpha, j)>TH1$ and $P(i+\beta, j)-P(i, j)>TH2$, where TH1 is a predetermined threshold (positive number), the object point indicates a black spot with the binarization function value $PD(i, j)$ for use in detecting a defect at the object point set to 1. Otherwise, the object point indicates a normal point with the binarization function value $PD(i, j)$ set to 0.

Generally, the number of containers of, for example, food is very large per time unit in a checking process. If a defect has been detected in a container tester in a production line, then a quick action should be taken to stop the production line. Otherwise, a large number of defective containers can be produced in a short time, thereby causing a serious problem of recovery of the production line. In this case, a longer recovery time requires a larger amount of financial loss correspondingly.

On the other hand, an illuminator which is used to stabilize a test image can be an element of the reliability of determination. That is, the brightness of the light of the illuminator may be lowered as time passes, and has undesired influence on precision. Generally, a test container is captured by a camera using a strobo flashbulb as a light source while it is being conveyed. However, the strobo flashbulb shows an uneven deterioration in brightness and the relationship between the number of flashes and deterioration cannot be calculated exactly.

Therefore, a strobo flashbulb is replaced with a new one at predetermined intervals so that the tester can be appropriately maintained. However, the strobo flashbulb costs rather high, and a unit for properly notifying a user of a timely replacement is earnestly demanded.

Regarding a defective illuminator, a defect can be easily detected, only if the illuminator provides no light at all, by detecting a black spot or a white spot inside a cylindrical container through fixed or difference binarization. However, if the test precision has been lowered through deterioration of brightness, then the tester could recognize all test objects as acceptable containers. In this case, there may arise a serious problem that no correct check is made until an operator recognizes the malfunction of the illuminator.

Frequent periodical maintenance of an illuminator for its strobo flashbulb to reduce such problems requires a high cost.

SUMMARY OF THE INVENTION

Based on the above described background, the present invention monitors the operation of an illuminator by constantly monitoring the brightness of a test image. When an abnormal condition exists, it is quickly notified to an external unit to reduce a financial loss in the container production and also to inform a user of a timely replacement for strobo flashbulb of the illuminator. Thus, the present invention realizes an image testing device to successfully reduce its maintenance cost.

The image testing device comprises a unit for generating a brightness measure area in an image area of a test object each time it is determined whether or not the test object is a defective product, obtaining the brightness of the picture elements from their average gray level in the brightness measure area, and correcting the binarization threshold, used in detecting a picture element indicating a defective portion of the test object, in proportion to the measured brightness.

The image testing device also comprises a first abnormal brightness determination unit for determining a preliminary abnormal brightness when the measured brightness is smaller than a predetermined abnormal brightness threshold, and for determining that an abnormal brightness has arisen if the preliminary abnormal brightness has been detected continuously for predetermined times (hereinafter referred to as a continuous abnormal brightness threshold).

The image testing device also comprises a second abnormal brightness determination unit for determining an abnormal brightness when the frequency of the preliminary abnormal brightness, as an average value of the occurrences of the preliminary abnormal brightness of the test object, is larger than a predetermined threshold. It further comprises an abnormal brightness occurrence signal output unit for outputting an abnormal brightness occurrence signal (for example, an alarm) according to the determination of an occurrence of an abnormal brightness made by both or either of the first and second abnormal brightness determination units.

The image testing device further defines plural sets of the abnormal brightness thresholds and continuous abnormal brightness thresholds, and determines an occurrence of an abnormal brightness made on each set of the abnormal brightness thresholds for each test object by the first and second abnormal brightness determination units. The above described abnormal brightness occurrence signal output unit outputs an abnormal brightness occurrence signal variable depending on the level of the deterioration of the intensity of a light source such as a strobo flashbulb.

BRIEF DESCRIPTION OF THE DRAWINGS

One skilled in the art can easily understand additional features and objects of this invention from the description of the preferred embodiments and some of the attached drawings. In the drawings:

FIGS. 1A and 1B shows the method of checking a cylindrical container;

FIGS. 2A and 2B shows the distribution of the variation of the brightness;

FIGS. 7A and 7B shows the brightness measure area in an image of a cylindrical container;

DESCRIPTION OF THE PREFERRED EMBODIMENTS

Figure 3:
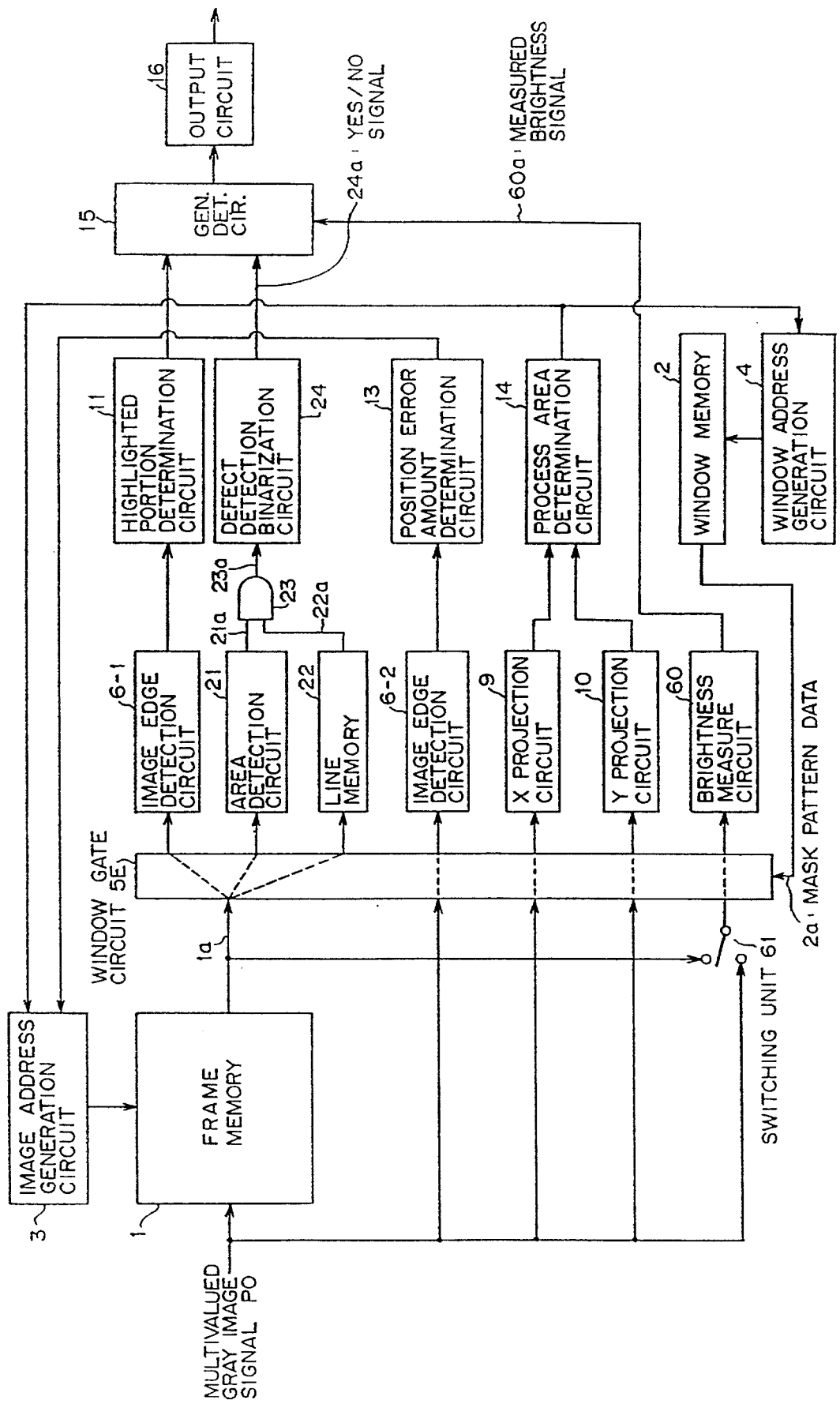
FIG. 3 is a block diagram showing the hardware of the cylindrical container inner surface tester as an embodiment of the present invention.

FIG. 3 is a block diagram showing the hardware of the cylindrical container inner surface tester and shows an embodiment of the present invention. In FIG. 3, a multivalued (for example, 8-bit) gray image signal PO is obtained by A/D converting a video signal obtained by raster-scanning the image on a TV camera not shown in FIG. 3; a frame memory 1 receives and stores the multivalued gray image signal PO as multivalued screen data; and an image address generation circuit 3 generates an address of the frame memory 1.

A window memory 2 stores mask pattern data for each window, that is, various types of ring-shaped window patterns concentric corresponding to the brightness patterns depending on the form of a container.

A window address generation circuit 4 generates an address of the window memory 2. The window gate circuit 5E masks the multivalued gray image signal PO or a multivalued gray image signal 1a read from the frame memory 1 with mask pattern data 2a so that only a specified multivalued gray image signal PO or 1a can be selectively passed.

Image edge detection circuits 6-1 and 6-2 detect the edges of an image, that is, the outer contour (outer circumference) and the inner contour (inner circumference) of a ring-shaped highlighted opening. An input image signal is binarized using a predetermined threshold used to detect the position of a test image and to check the circularity of the contour of a container. The coordinates of the rise and fall points (referring to image edges) of the binarized signal are stored in the memories of the image edge detection circuits 6-1 and 6-2. A highlighted portion determination circuit 11 checks the circularity of the contour of a container with reference to the outer or inner circumference detected by the image edge detection circuit 6-1, and provides the check result to the general determination circuit 15.

To generate a window at a correct position relative to a test object, the image edge detection circuit 6-2 receives the latest multivalued gray image signal PO, and a position error amount determination circuit 13 detects an error between the center position of the actual test image detected from an image edge and that of a predetermined window.

An area detection circuit 21 receives the multivalued gray image signal 1a which passes through the window gate circuit 5E from the frame memory 1, and outputs an area detection signal 21a as a signal indicating the test area where a defective point has been detected for each horizontal scanning line (that is, an area segmented by the contour of the test container).

A line memory 22 receives and temporarily stores the multivalued gray image signal 1a in horizontal scanning line units synchronously with the area detection circuit 21.

An AND circuit 23 ANDs the area detection signal 21a and a gray image signal 22a output from the line memory 22 as an image signal for each horizontal scanning line corresponding to the area detection signal 21a. It then outputs a gray image signal (referred to as a test area gray image signal) 23a of only defective test area. The AND gate 23 correctly deletes a gray image signal of the portion generated externally to the contour of the test container even if a distortion of the contour of the test container is detected by a position error of the center of the container from the center of the image.

A defect detection binarization circuit 24 detects a picture element indicating a defective portion. The defect detection binarization circuit 24 binarizes the test area gray image signal 23a using a fixed binarization threshold (that is, a threshold according to the fixed binarization method) preliminarily set for each window area, or (and) it binarizes the difference in brightness between the object picture element of the test area gray image signal 23a and its background picture element using a predetermined difference binarization threshold (that is, a threshold according to the difference binarization method). The AND gate 23 and the defect detection binarization circuit 24 are binarization circuits for extracting a picture element indicating a defective point. The defect detection binarization circuit 24 further counts the number of binarized picture elements indicating defective points as a defective area value.

Figure 4:
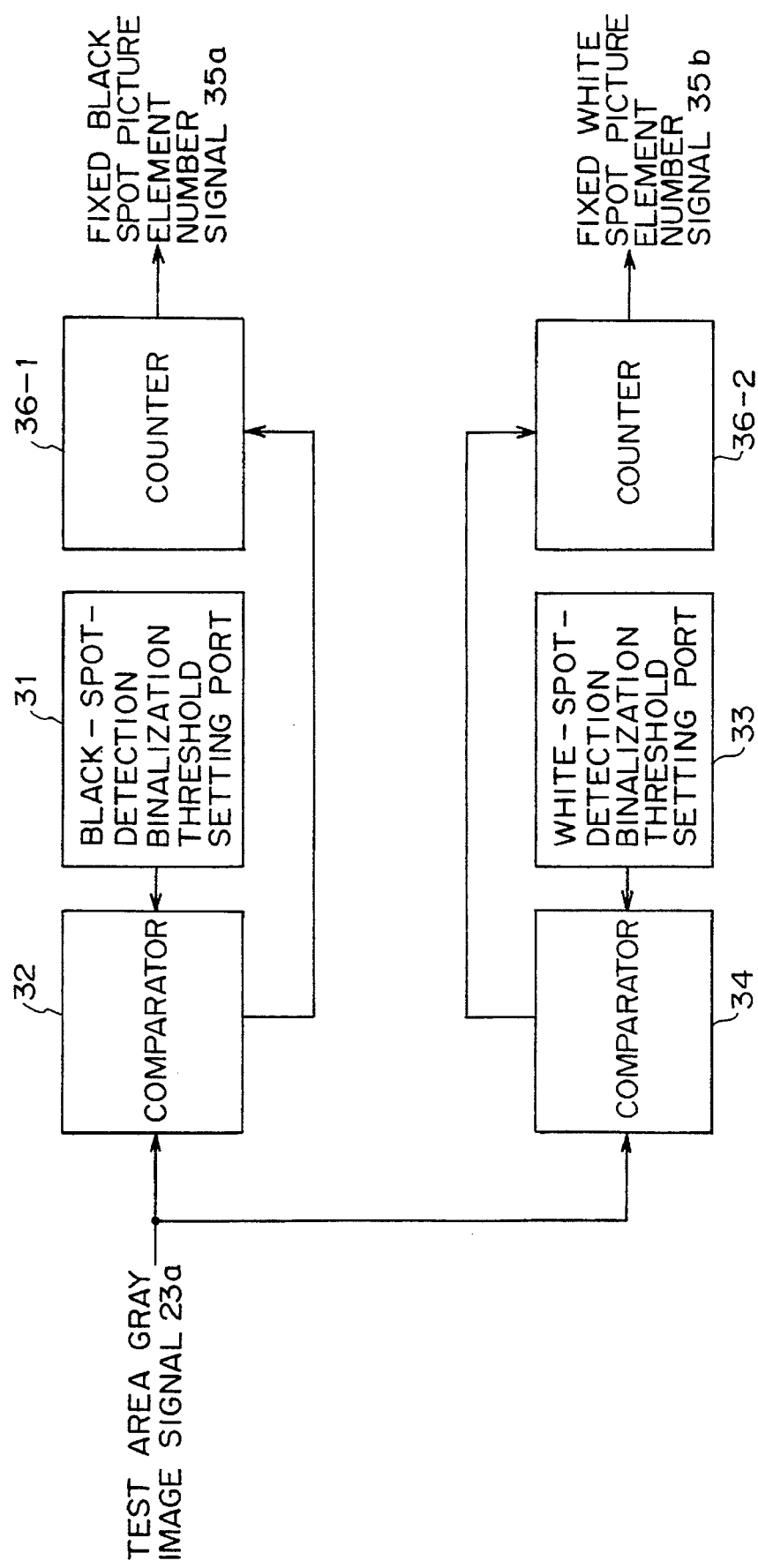
FIG. 4 is a block diagram showing the configuration of the fixed binarization and defect detection circuit in the defect detecting binarization circuit shown in FIG. 3.

FIG. 4 is the block diagram showing the configuration of the fixed binarization and defect detection circuit 241 forming part of the defect detection binarization circuit 24. In FIG. 4, a comparator 32 compares the test area gray image signal 23a with the value of a black-spot-detection binarization threshold setting port 31 for setting a first black level. The comparison result (a picture element of the brightness smaller than the first black level) is provided as a count signal for a counter 36-1. The number of fixed black spot picture elements are counted. Thus, a fixed black spot picture element number signal 35a is output.

On the other hand, a comparator 34 compares the test area gray image signal 23a with the value of a white-spot-detection binarization threshold setting port 33 for setting a first white level. The comparison result (a picture element of the brightness larger than the first white level) is provided as a count signal for a counter 36-2. The number of fixed white spot picture elements are counted. Thus, a fixed white spot picture element number signal 35b is output.

Figure 5:
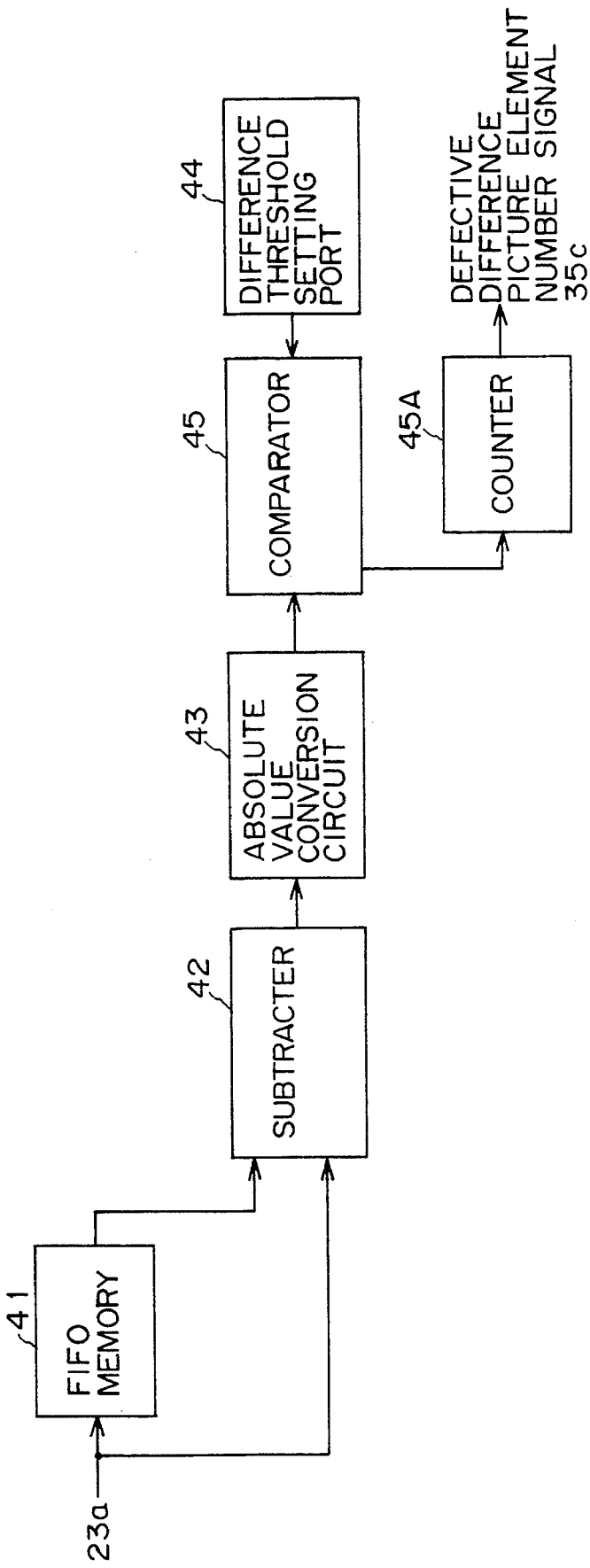
FIG. 5 is a block diagram showing the configuration of the difference binarization and defect detection circuit in the defect detecting binarization circuit shown in FIG. 3.

FIG. 5 is the block diagram showing the configuration of the difference binarization and defect detection circuit 242 forming part of the defect detection binarization circuit 24. In FIG. 5, a FIFO memory 41 temporarily stores the test area gray image signal 23a. The FIFO memory 41 provides a signal delayed by a predetermined number of picture elements (that is, a background picture element signal) for a subtracter 42. The subtracter 42 directly receives the test area gray image signal 23a (that is, an object picture element signal), and subtracts the brightness of the object picture element from the brightness of the background picture element. The subtraction result is output to an absolute value conversion circuit 43.

The absolute value conversion circuit 43 checks a sign bit of the received subtraction result. If it is negative, it is converted into a positive value. Then, a comparator 45 compares the output (difference signal) of the absolute value conversion circuit 43 with the first difference level set by a difference threshold setting port 44. The comparison result (a picture element of the difference larger than the first difference level) is provided as a count signal for a counter 45A. The number of picture elements indicating defective points are counted. Thus, a defective difference picture element number signal 35c is output.

Figure 6:
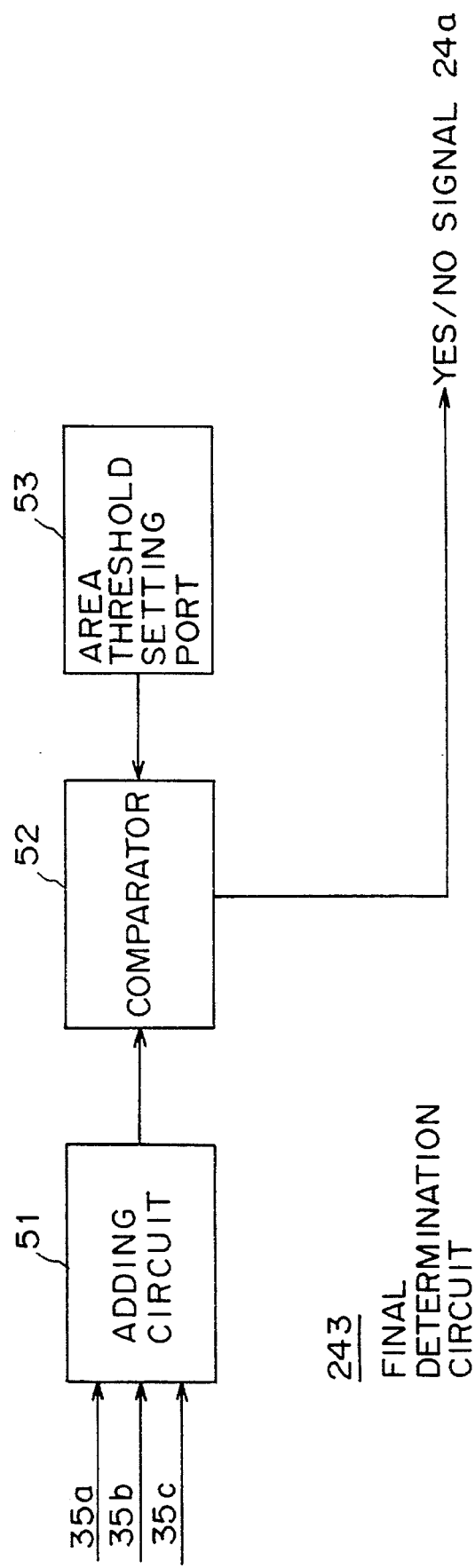
FIG. 6 is a block diagram showing the configuration of the final determination circuit in the defect detecting binarization circuit shown in FIG. 3.

FIG. 6 is the block diagram showing the configuration of the final determination circuit 243 forming the remaining part of the defect detection binarization circuit 24. In FIG. 6, an addition circuit 51 calculates a total of the defect indicating picture element number signals 35a, 35b, and 35c. A comparator 52 compares the defect indicating picture element sum area with the first area threshold set in an area threshold setting port 53 for each window area. Thus, the result is output as the Yes/No signal 24a from the comparator 52 to the general determination circuit 15 shown in FIG. 3.

The CPU sets necessary data required to set the first black level, first white level, first difference level, first area threshold, etc. at respective setting points.

The peak/valley detecting binarization circuit disclosed in Tokugan-hei 3-265134 by the Inventor of the present invention is included in the method of detecting a defective point by the difference binarization shown in FIGS. 7A and 7B. This circuit determines that an object picture element indicates a defective point if two differences obtained by subtracting the value of the object picture element according to the test area gray image signal 23a in a screen scanning line from the values of the background picture elements the equal number of elements (hereinafter referred to as an a picture elements) before and after the object picture element (hereinafter referred to respectively as a antecedent and subsequent background picture elements) indicate the same polarity, and if one of the two absolute values is larger than a predetermined first threshold of the polarity and the other absolute value is larger than a predetermined second threshold of the polarity.

The brightness measure circuit 60 shown in FIG. 3 is the most important unit of the present invention, and uses a brightness measure area (for example, 150 shown in FIG. 7A) stored in the window memory 2 as a gate area. FIG. 7A shows the circular brightness measure area 150 set in the inner surface of a container. The image testing device according to the present invention determines the brightness of a test image. In this case, the brightness of the test image is determined by calculating an average gray level value of some sampled picture elements, not by calculating the gray levels of all picture elements.

The brightness is measured with sufficient stability by correctly positioning the brightness measure area 150 when the picture elements are extracted such that the coordinate of the center of the brightness measure area 150 matches that of the center of the captured image of the bottom inner surface.

Then, the binarization threshold, which is used in detecting picture elements as black and white spots on a test object, is corrected to vary in proportion to the brightness so as to reduce the precision of a test.

If the measured brightness is monitored and it is smaller than a predetermined threshold more frequently than a predetermined value, the image testing device outputs an alarm to properly maintain the illuminator. The brightness measure circuit 60 fetches through the window gate circuit 5E the multivalued gray image signal PO selected by the switching unit 61 or the multivalued gray image signal 1a from the frame memory 1 whichever is included in the gate area. The selected signal is sent to the brightness measure circuit 60 as an input signal to calculate a total of gray level values of picture elements input to the brightness measure circuit 60.

Figure 8:
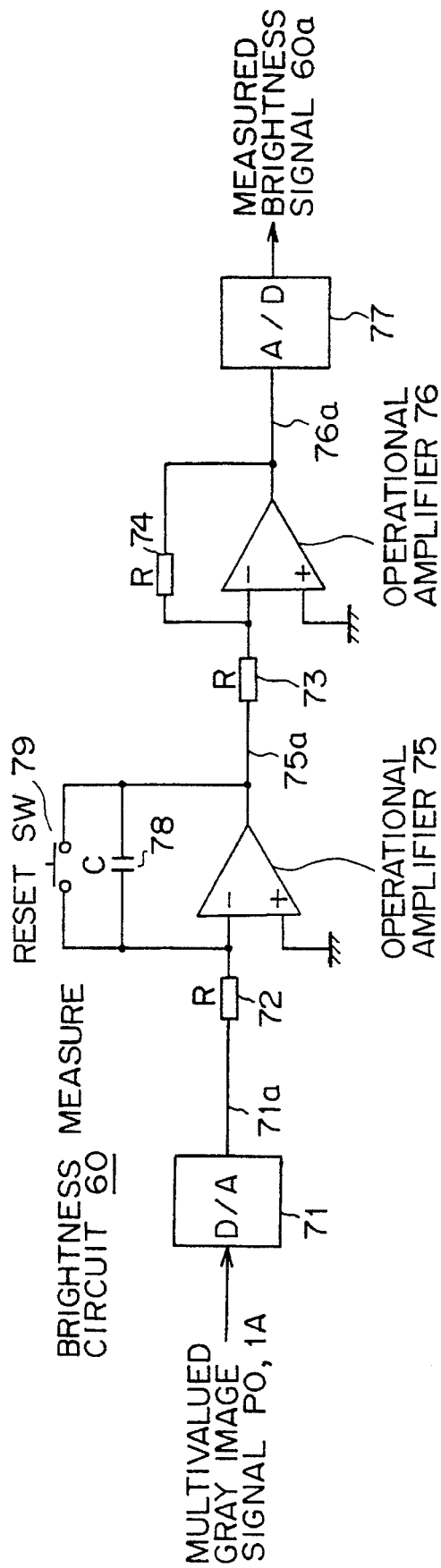
FIG. 8 is a block diagram showing the configuration of the brightness measure circuit shown in FIG. 3.

FIG. 8 shows an example of the brightness measure circuit 60. The brightness measure circuit 60 converts the input digital gray image signal (PO or 1a) into an analog signal 71a through a D/A converter 71. The analog signal 71a is integrated by an integrator comprising a resistor 72, capacitor 78, operational amplifier 75, and a reset switch 79. The output of the integrator (minus signal) 75a is input to an inverter comprising resistors 73 and 74 and an operational amplifier 76 and inverted into a plus signal output 76a. The signal 76a is re-converted into a digital signal by an A/D converter 77, and output as the measured brightness signal 60a to the general determination circuit 15 shown in FIG. 3.

The general determination circuit 15 compares the measured brightness signal 60a with an abnormal brightness threshold. If the measured brightness signal 60a is smaller than the abnormal brightness threshold, then a preliminary abnormal brightness counter is incremented by 1. If the measured brightness signal 60a is larger than the abnormal brightness threshold, then a preliminary abnormal brightness counter is cleared to 0. Thus, a preliminary abnormal brightness repetition is obtained. That is, if a preliminary abnormal brightness has arisen, the count value corresponding to the number of determinations can be read from the preliminary abnormal brightness counter.

Then, the general determination circuit 15 comprises a first abnormal brightness determination unit for comparing the value of the preliminary abnormal brightness counter with the abnormal brightness repetition threshold. If the value of the preliminary abnormal brightness counter is larger than the abnormal brightness repetition threshold, the first abnormal brightness determination unit determines an abnormal brightness.

The general determination circuit 15 further comprises a second abnormal brightness determination unit for calculating a rate with a predetermined number of determinations made on a test object set as a denominator and a number of determinations causing the preliminary abnormal brightness set as a numerator, for obtaining an average value of the rate variable as the determinations proceeds, and for determining an abnormal brightness when a preliminary abnormal brightness occurrence rate is larger than the threshold preliminarily set in the image testing device.

Then, the general determination circuit 15 instructs the output circuit 16 shown in FIG. 3 to generate an abnormal brightness signal according to the condition of a logical sum of the outputs of abnormal brightness determinations from the first and second abnormal brightness determination units. As described above, the CPU not shown in the drawings sets necessary data required to set the first black, white, difference, area thresholds, etc. However, in the present invention, these thresholds are corrected by the CPU according to the measured brightness signal 60a as follows.

That is, the thresholds (hereinafter referred to as an initially-set threshold group) are set when the first black, white, and difference levels (hereinafter referred to generally as a threshold group) are selected for each window area and stored together with the measured brightness (the value of the measured brightness signal 60a, and hereinafter referred to as initially-set brightness). When a cylindrical container is checked in an online operation, the brightness measure circuit 60 obtains a measured brightness (hereinafter referred to as a determined measured brightness) of a test image, and a determined threshold group is calculated and corrected by the CPU not shown in the drawings.

$$\text{(determined threshold group)/(initially-set threshold group)=(determined measured brightness)/(initially-set measured brightness)} \quad (1)$$

Thus, the precision in defect detection can be reduced by correcting a defect detection threshold in proportion to the reduction of the brightness of the illuminator.

The abnormal brightness threshold and the abnormal brightness repetition threshold can be set more than once. That is, each abnormal brightness threshold is set under the condition of abnormal brightness threshold #1>abnormal brightness threshold #2>abnormal brightness threshold #3 . . . Likewise, each abnormal brightness repetition threshold is set under the condition of abnormal brightness repetition threshold #1>abnormal brightness repetition threshold #2>abnormal brightness repetition threshold #3 . . . . For each set of the abnormal brightness threshold and the abnormal brightness repetition threshold having the same number #1, #2, #3, . . . , each abnormal brightness signal #1, #2, #3, . . . can be generated under the condition of the logical sum of the first and second abnormal brightness determination units.

Thus, since the brightness of the light source deteriorates as time passes, the abnormal brightness signals #1, #2, #3, . . . sequentially, and the deterioration level of the light source can be correctly informed. Accordingly, an appropriate maintenance can be provided for the light source.

According to the present invention, a binarization threshold measure area is set in an image of a test object, and an average brightness of the gray level of the image is measured. Then, the binarization threshold, which is used in detecting picture elements as black and white spots on a test object, is corrected to vary in proportion to the brightness so as to reduce the precision of a test.

If the measured brightness is monitored and it is smaller than a predetermined threshold more frequently than a predetermined value, the image tester outputs an alarm to properly maintain the illuminator.

What is claimed is:

1. An image testing device for detecting a defect in a test object by capturing an illuminated inner surface of a test object illuminated by an illuminating means and analyzing a captured image, wherein a predetermined fixed and difference binarization threshold is set for use in detecting a picture element indicating a black spot and a white spot; obtained is a total of picture elements indicating defective points binarized for each image area using the binarization threshold; and it is determined whether or not the test object is defective depending on a comparison between a number of picture elements indicating defective points and an area threshold for detection of a defective object in each image area, said tester comprising:

means for generating a brightness measure area in an image area of the test object for each determination, obtaining an average gray level (hereinafter referred to as the measured brightness) of all or a part of the brightness measure area, and for correcting the binarization threshold in proportion to the measured brightness;

abnormal brightness determination means for determining a preliminary abnormal brightness by detecting that the measured brightness is smaller than a predetermined abnormal brightness threshold, and for determining that an abnormal brightness has arisen if the preliminary abnormal brightness has been detected more than predetermined times (hereinafter referred to as an abnormal brightness repetition threshold); and means for outputting an abnormal brightness signal based on a determination of abnormal brightness determination means.

2. The image testing device according to claim 1, wherein plural sets of the abnormal brightness thresholds and abnormal brightness repetition thresholds are set;

said abnormal brightness occurrence signal output means outputs an abnormal brightness occurrence signal according to a determination of an occurrence of the abnormal brightness made on each set of the abnormal brightness thresholds for each test object by said abnormal brightness determination means.

3. The image testing device according to claim 1, wherein the test object is a cylindrical container actually symmetrical to axis; and the illuminating means is ring-shaped concentric with the cylindrical container and illuminates the inner surface of the cylindrical container.

4. An image testing device for detecting a defect in a test object by capturing an illuminated inner surface of a test object illuminated by an illuminating means and analyzing a captured image, wherein a predetermined fixed and difference binarization threshold is set for use in detecting a picture element indicating a black spot and a white spot; obtained is a total of picture elements indicating defective points binarized for each image area using the binarization threshold; and it is determined whether or not the test object is defective depending on a comparison between a number of picture elements indicating defective points and an area threshold for detection of a defective object in each image area, said tester comprising:

means for generating a brightness measure area in an image area of the test object for each determination, obtaining an average gray level (hereinafter referred to as the measured brightness) of all or a part of the brightness measure area, and for correcting the binarization threshold in proportion to the measured brightness;

first abnormal brightness determination means for determining a preliminary abnormal brightness by detecting that the measured brightness is smaller than a predetermined abnormal brightness threshold, and for determining that an abnormal brightness has arisen if the preliminary abnormal brightness has been detected more than predetermined times (hereinafter referred to as an abnormal brightness repetition threshold);

second abnormal brightness determination means for determining the abnormal brightness by detecting that a frequency of the preliminary abnormal brightness, which is an average value of occurrences of the preliminary abnormal brightness of the test object, is larger than a predetermined threshold; and means for outputting an abnormal brightness signal based on said second abnormal brightness determination means.

5. The image testing device according to claim 4, wherein plural sets of the abnormal brightness thresholds and abnormal brightness repetition thresholds are set;

said abnormal brightness occurrence signal output means outputs an abnormal brightness occurrence signal according to a determination of an occurrence of the abnormal brightness made on each set of the abnormal brightness thresholds for each test object by said first abnormal brightness determination means and said second abnormal brightness determination means.

6. The image testing device according to claim 4, wherein the test object is a cylindrical container actually symmetrical to axis; and the illuminating means is ring-shaped concentric with the cylindrical container and illuminates the inner surface of the cylindrical container.

7. An image testing device for detecting a defect in a test object by capturing an illuminated inner surface of a test object illuminated by an illuminating means and analyzing a captured image, wherein a predetermined fixed and difference binarization threshold is set for use in detecting a picture element indicating a black spot and a white spot; obtained is a total of picture elements indicating defective points binarized for each image area using the binarization threshold; and it is determined whether or not the test object is defective depending on a comparison between a number of picture elements indicating defective points and an area threshold for detection of a defective object in each image area, said tester comprising:

means for generating a brightness measure area in an image area of the test object for each determination, obtaining an average gray level (hereinafter referred to as the measured brightness) of all or a part of the brightness measure area, and for correcting the binarization threshold in proportion to the measured brightness;

first abnormal brightness determination means for determining a preliminary abnormal brightness by detecting that the measured brightness is smaller than a predetermined abnormal brightness threshold, and for determining that an abnormal brightness has arisen if the preliminary abnormal brightness has been detected more than predetermined times (hereinafter referred to as an abnormal brightness repetition threshold);

second abnormal brightness determination means for determining the abnormal brightness by detecting that a frequency of the preliminary abnormal brightness, which is an average value of occurrences of the preliminary abnormal brightness of the test object, is larger than a predetermined threshold; and means for outputting an abnormal brightness signal based on said first abnormal brightness determination means and said second abnormal brightness determination means.

8. The image testing device according to claim 7, wherein plural sets of the abnormal brightness thresholds and abnormal brightness repetition thresholds are set;

said abnormal brightness occurrence signal output means outputs an abnormal brightness occurrence signal according to a determination of an occurrence of the abnormal brightness made on each set of the abnormal brightness thresholds for each test object by said first abnormal brightness determination means and said second abnormal brightness determination means.

9. The image testing device according to claim 7, wherein the test object is a cylindrical container actually symmetrical to axis; and the illuminating means is ring-shaped concentric with the cylindrical container and illuminates the inner surface of the cylindrical container.

* * * * *

UNITED STATES PATENT AND TRADEMARK OFFICE
CERTIFICATE OF CORRECTION

PATENT NO. : 5,608,815
DATED : Mar. 4, 1997
INVENTOR(S) : Toyama et al.

It is certified that error appears in the above-indentified patent and that said Letters Patent is hereby corrected as shown below:

On the Title Page:

Under "[56] References Cited for U.S. Patent Documents", delete "4,972,393" and insert -- 4,972,093--.

Column 6, line 22, delete "a" and insert --$\alpha$--.

Signed and Sealed this

Fourteenth Day of October, 1997

*Attest:*

BRUCE LEHMAN

*Attesting Officer*  *Commissioner of Patents and Trademarks*